US009238103B2

(12) United States Patent
Jakob et al.

(10) Patent No.: US 9,238,103 B2
(45) Date of Patent: Jan. 19, 2016

(54) LIQUID TRANSFER DEVICE FOR MEDICAL DISPENSING CONTAINERS

(75) Inventors: Laurent Jakob, Bernex-Suisse (CH); Frederic Rivas, Grand-Lancy (FR)

(73) Assignee: Bracco Suisse S.A., Manno (CH)

( * ) Notice: Subject to any disclaimer, the term of this patent is extended or adjusted under 35 U.S.C. 154(b) by 1194 days.

(21) Appl. No.: 12/086,310

(22) PCT Filed: Dec. 5, 2006

(86) PCT No.: PCT/EP2006/069336
§ 371 (c)(1),
(2), (4) Date: Jun. 10, 2008

(87) PCT Pub. No.: WO2007/068633
PCT Pub. Date: Jun. 21, 2007

(65) Prior Publication Data
US 2009/0159485 A1    Jun. 25, 2009

(30) Foreign Application Priority Data
Dec. 16, 2005    (EP) ..................... 05112319

(51) Int. Cl.
*A61J 1/20*    (2006.01)
*A61M 5/162*    (2006.01)

(52) U.S. Cl.
CPC .............. *A61M 5/162* (2013.01); *A61J 1/2089* (2013.01); *A61J 1/201* (2015.05); *A61J 1/2075* (2015.05); *A61J 1/2082* (2015.05); *A61J 1/2096* (2013.01); *A61M 2005/1623* (2013.01)

(58) Field of Classification Search
CPC ............ A61J 1/2089; A61J 2001/2068; A61J 2001/2072; A61J 2001/2075; A61M 2005/1623
USPC ........... 137/268, 588; 604/411, 412, 413, 414
See application file for complete search history.

(56) References Cited

U.S. PATENT DOCUMENTS

| 3,797,521 | A |   | 3/1974 | King |
|---|---|---|---|---|
| 4,203,436 | A |   | 5/1980 | Grimsrud |
| 4,262,671 | A | * | 4/1981 | Kersten ......................... 604/251 |
| 4,543,101 | A | * | 9/1985 | Crouch ......................... 604/411 |
| 4,623,343 | A |   | 11/1986 | Thompson |
| 4,675,004 | A |   | 6/1987 | Hadford et al. |
| 4,787,898 | A | * | 11/1988 | Raines ......................... 604/411 |
| 4,857,068 | A |   | 8/1989 | Kahn |

(Continued)

FOREIGN PATENT DOCUMENTS

DE    29617329 U1    2/1997
EP    0240144 A1    7/1987

(Continued)

OTHER PUBLICATIONS

PCT International Search Report for PCT/EP2006/069336, mail date Mar. 6, 2007.

(Continued)

*Primary Examiner* — Kevin Murphy
(74) *Attorney, Agent, or Firm* — Vivicar Law, PLLC (57) ABSTRACT

A kit comprising a medical dispensing container (402), such as a vial for diagnostic agents, and a liquid transfer device (401) to be used to transfer a liquid into or from said dispensing container. The transfer device allows substantially limiting the gaseous exchange between the inside of a vial and the external ambient, when the device is connected to the vial in steady state conditions.

22 Claims, 8 Drawing Sheets

(56) References Cited

U.S. PATENT DOCUMENTS

| | | | |
|---|---|---|---|
| 5,041,106 A | 8/1991 | Noji et al. | |
| 5,271,928 A | 12/1993 | Schneider et al. | |
| 5,413,774 A | 5/1995 | Schneider et al. | |
| 5,445,813 A | 8/1995 | Schneider et al. | |
| 5,556,610 A | 9/1996 | Yan et al. | |
| 5,597,549 A | 1/1997 | Schneider et al. | |
| 5,636,660 A * | 6/1997 | Pfleiderer et al. | 137/550 |
| 5,711,933 A | 1/1998 | Bichon et al. | |
| 5,827,504 A | 10/1998 | Yan et al. | |
| 6,139,534 A * | 10/2000 | Niedospial et al. | 604/411 |
| 6,333,021 B1 | 12/2001 | Schneider et al. | |
| 6,635,885 B2 * | 10/2003 | McCauley et al. | 250/428 |
| 6,743,214 B2 | 6/2004 | Heil et al. | |
| 2001/0008626 A1 * | 7/2001 | Schneider et al. | 424/9.52 |
| 2003/0229330 A1 * | 12/2003 | Hickle | 604/411 |

FOREIGN PATENT DOCUMENTS

| | | |
|---|---|---|
| EP | 0554213 A1 | 4/1993 |
| EP | 1228770 A1 | 8/2002 |
| EP | 0682530 B1 | 3/2003 |
| EP | 1228770 B1 | 7/2005 |
| GB | 486442 A | 6/1938 |
| JP | 60-141837 A | 7/1985 |
| JP | 62-253069 A | 11/1987 |
| JP | 5-255127 A | 10/1993 |
| JP | 11-503627 A | 3/1999 |
| WO | 94/09829 A1 | 5/1994 |
| WO | WO 95/16467 A1 | 6/1995 |
| WO | 96/29113 A1 | 9/1996 |
| WO | WO 97/29783 A1 | 8/1997 |
| WO | WO 03/043564 A1 | 5/2003 |
| WO | WO 2004/069284 A2 | 8/2004 |
| WO | WO 2004/069284 A3 | 8/2004 |
| WO | WO 2006/128500 A1 | 12/2006 |

OTHER PUBLICATIONS

PCT Written Opinion of the ISA for PCT/EP2006/069336, mail date Mar. 6, 2007.
PCT International Preliminary Report on Patentability for PCT/EP2006/069336, mail date Jun. 26, 2008.
Office Action for Australian application No. 2006326148, mail date Oct. 19, 2011.
Office Action for Australian application No. 2006326148, mail date Oct. 23, 2012.
Office Action for Canadian application No. 2,629,252, mail date Mar. 14, 2013.
Office Action for Japanese application No. 2008-544964, mail date Jul. 26, 2011 (English Translation).
Office Action for Korean application No. 10-2008-7014542, mail date May 22, 2013 (English Translation).

* cited by examiner

LIQUID TRANSFER DEVICE FOR MEDICAL DISPENSING CONTAINERS

This application is the national stage application of corresponding international application number PCT/EP2006/069336 filed Dec. 5, 2006, which claims priority to and the benefit of the European application no. 05112319.8, filed Dec. 16, 2005, all of which are hereby incorporated by reference.

TECHNICAL FIELD

The invention relates to a liquid transfer device to be used to transfer a liquid into or from a dispensing container, particularly a medical dispensing container like a vial for diagnostic agents and to a pharmaceutical kit comprising said device and said container.

BACKGROUND OF THE INVENTION

Medical dispensing containers made of glass or polymeric materials, the walls of which are non-collapsible, typically require an air inlet when a medical fluid is withdrawn therefrom, to prevent the formation of vacuum therein. Typically, vials containing a medical fluid are closed by rubber stoppers which are pierced by a spike of a transfer device having a duct for the passage of the medical fluid and a ventilation duct. Examples of devices comprising a liquid fluid duct and a ventilation duct are disclosed, for instance, in U.S. Pat. No. 3,797,521, U.S. Pat. No. 4,262,671, U.S. Pat. No. 4,623,343, U.S. Pat. No. 4,857,068, U.S. Pat. No. 5,041,106, and U.S. Pat. No. 6,139,534.

The present invention is particularly concerned with the liquid transfer into a container containing a medicament reconstitutable upon addition of said liquid, and the subsequent removal of the reconstituted medicament from said container. More particularly, the device of the invention is suitable for the preparation and dispensing of some diagnostic or therapeutic agents, such as those comprising a gaseous component including, for instance, gas-filled microvesicles for ultrasound diagnostic and/or therapeutic use.

Gas-filled microvesicles for ultrasound diagnostic and/or therapeutic use include suspensions of gas bubbles having a diameter of a few microns dispersed in an aqueous medium. Of particular interest are gas bubbles which are stabilized by means of suitable additives such as, for example emulsifiers, oils, thickeners or sugars, or by entrapping or encapsulating the gas or a precursor thereof in a variety of systems. These agents are designed to be used primarily as intravenous or intra-arterial injectables in conjunction with the use of medical echographic equipment which employs for example, B-mode image formation (based on the spatial distribution of backscatter tissue properties) or Doppler signal processing (based on Continuous Wave or pulsed Doppler processing of ultrasonic echoes to determine blood or liquid flow parameters).

A first category of stabilized bubbles or microvesicles is generally referred to in the art as "microbubbles" and includes aqueous suspensions in which the bubbles of gas are bounded at the gas/liquid interface by a very thin envelope (film) involving a stabilizing amphiphilic material disposed at the gas to liquid interface. Microbubble suspensions are typically prepared by contacting powdered amphiphilic materials, e.g. freeze-dried preformed liposomes or freeze-dried or spray-dried phospholipid solutions, with air or other gas and then with an aqueous carrier, while agitating to generate a microbubble suspension which can then be administered.

Examples of aqueous suspension of gas microbubbles and preparation thereof are disclosed, for instance, in U.S. Pat. No. 5,271,928, U.S. Pat. No. 5,445,813, U.S. Pat. No. 5,413,774, U.S. Pat. Nos. 5,556,610, 5,597,549, U.S. Pat. No. 5,827,504, WO 97/29783 and WO 04/069284.

Commercially available ultrasound contrast agents of this type include for instance SonoVue® (Bracco International BV).

A second category of microvesicles is generally referred to in the art as "microballoons" or "microcapsules" and includes suspensions in which the bubbles of gas are surrounded by a solid material envelope of a lipid or of natural or synthetic polymers. Examples of microballoons and of the preparation thereof are disclosed, for instance, in U.S. Pat. No. 5,711,933 and U.S. Pat. No. 6,333,021.

Whilst the above formulations are administered as suspensions of gas-filled microvesicles in a suitable physiologically acceptable liquid, for storage purposes it is in general preferred to use precursors of said microvesicles in dry (e.g. lyophilized) form, as disclosed in the above mentioned patents and patent applications. The microvesicles suspension is then obtained by adding to said dry precursors, in the presence of a suitable gas (e.g a fluorinated gas), a physiologically acceptable liquid carrier, preferably under agitation. The dry precursor can for instance be stored in a vial (e.g. of glass) in the presence of a desired gas, said vial being sealed with a suitable stopper (e.g. of rubber), through which the liquid carrier can be injected. The contrast agent formulation can thus be supplied in a kit comprising a vial (containing the dry precursor and the gas) and a pre-filled syringe (containing the physiologically acceptable liquid carrier). The syringe can be associated with a suitable liquid transfer device which typically comprises a spike for piercing the stopper, a first conduit for injecting the liquid carrier into the vial and withdrawing the formed microbubbles suspension from it, and a second conduit (vent tube) for allowing a gas/air flow from and into the container during the respective liquid injection and withdrawal phases. Examples of such devices are disclosed, for instance, in U.S. Pat. No. 6,743,214.

When the suspension of gas-filled microbubbles has been reconstituted with the addition of the liquid, it may however be desirable to keep said reconstituted suspension in the vial for a relatively long time (e.g. few hours) before using. As observed by the Applicant, such a relatively long storage time of the reconstituted suspension may however pose some problems, particularly in connection with a possible exchange between the gas contained inside the container and the outer atmosphere air. This may be for instance the case when a liquid transfer device (such as the one disclosed in U.S. Pat. No. 6,743,214) is employed, where a direct fluid-gas passage is present between the inside of the container and the outer ambient, with consequent possible air inlet inside the container. While it has been demonstrated that a fluorinated gases employed for filling the microvesicles can be admixed with relatively high amounts of air (e.g. up to 70-80% by volume of air) without substantially modifying the properties and stability of the gas-filled microvesicles (as described for instance in EP patent no. 682 530), an excessive amount of air may nevertheless negatively affect said properties and stability. In addition, when the gas filled microvesicles already contain a mixture of fluorinated gas and air (as in the above mentioned EP 682 530), the negative effects deriving by said air inlet may be more evident.

Furthermore, the above undesirable gas/air exchange may similarly take place also when the transfer device is connected to the vial and left in place for a certain time, without connecting a syringe thereto and/or injecting a liquid into the vial.

In co-pending International patent application PCT/EP2005/056975, the Applicant suggests to insert a suitable valve in the vent tube of the transfer device, so to substantially avoid said gaseous exchange under steady state conditions.

SUMMARY OF THE INVENTION

The Applicant has now observed that, for most practical cases, it is however not necessary to avoid said gaseous exchange under steady state conditions. As observed by the applicant, in practical applications it is in fact sufficient to substantially limit said gaseous exchange in steady state conditions over a limited period of time. The applicant has thus devised a new liquid transfer device capable of substantially limiting the gaseous exchange between said container and the outer ambient atmosphere. According to a preferred aspect of the invention, it has been observed that said gaseous exchange can be substantially limited by suitably dimensioning the vent tube of the transfer device, without the need of inserting any means (such as a valve) for physically interrupting the flow of gas through said conduit. In particular, said dimensioning comprises reducing the diameter and/or increasing the length of the vent tube with respect to conventional vent tubes.

The liquid transfer device of the invention is also preferably adapted to control the variation of the internal pressure of the container during the liquid injection or withdrawal phases.

A first aspect of the present invention relates to a pharmaceutical kit for the preparation of a medicament comprising:
  a) a medical dispensing container defining an inner space and containing a physiologically acceptable gas therein, and
  b) a liquid transfer device, which cooperates with said container for transferring a liquid into or from said container, said device comprising a first and a second conduit, said first and said second conduit allowing a fluid contact between the inner space and an external ambient when said device cooperates with said container, wherein:
     when said device cooperates with the container during a liquid flow into or from said dispensing container, said liquid flow is effected through said first conduit while said second conduit allows a gaseous flow between said container and an external ambient; and
     when said device cooperates with the container in steady state conditions, less than 20% (v/v) of the total volume of gas contained in said container is exchanged with the external ambient over a period of 6 hours in steady state conditions;
  said second conduit being substantially devoid of means for interrupting the flow of gas between said container and the external ambient.

Preferably, the gaseous exchange between said container and the external ambient in steady state conditions is substantially prevented for at least 6 hours. In particular, said gaseous exchange is preferably less than 10% (v/v) of the total volume of gas contained in said container, more preferably less than 5%, over a period of 6 hours.

Advantageously, said second conduit is dimensioned in such a way as to avoid any overpressure higher than 300 mbar inside said container during the liquid flow into said container.

Advantageously the transfer device comprises a filter associated to the second conduit, for protecting the content of the vial against microbial contamination during liquid withdrawal. Preferably, said filter also prevents the fluid to flow out from the container into the external ambient. Said filter is preferably a liquid impermeable/gas permeable filter. More preferably it is a hydrophobic filter.

According to a preferred embodiment said transfer device comprises a connector for connecting a fluid injector, such as a syringe, thereto. Preferably, said connector is a luer connector.

According to a preferred embodiment, said medical dispensing container comprises a pharmaceutically active formulation, diagnostic agent or nutritional formulation. The container is a rigid container, preferably a vial, e.g. of glass. The vial comprises a substantially cylindrical body, a flat bottom portion and a top portion defining an open area closed by a stopper hermetically sealing the content of the vials. The vial's content can be, for instance, a suspension of gas-filled microbubbles or microvesicles for diagnostic and/or therapeutic use or a precursor thereof, e.g. in the form of a dry lipid deposit, in contact with a physiologically acceptable gas.

A further aspect of the invention relates to a pharmaceutical kit comprising a liquid transfer device as above defined, a vial containing a pharmaceutically active formulation (e.g. a dry lipid deposit and a physiologically acceptable gas) and a syringe pre-filled with a physiologically acceptable (e.g. saline) solution. The liquid transfer device is used for injecting the solution into the vial and withdrawing the reconstituted medicament. The medicament is preferably a diagnostic agent, particularly an ultrasound contrast agent, to be administered as suspensions of gas-filled microvesicles or microbubbles in a physiologically acceptable liquid.

The characteristics of the invention and the advantages derived therefrom will appear more clearly from the following description of non limiting embodiments, illustrated in the annexed drawings.

DETAILED DESCRIPTION OF THE INVENTION

A liquid transfer device according to the invention allows to substantially limit the gaseous exchange between the inner volume of the container and the external atmosphere under steady state conditions (i.e. when the transfer device is connected to the container in the absence of any flow of liquid into or from said container). In particular, according to the present invention, the substantial limitation of gas exchange can be defined as a gaseous exchange which is of less than about 20% (v/v) of the total volume of the container over a period of time of 6 hours, preferably of less than about 10% and more preferably of less than 5%.

As observed by the Applicant, the gas exchange between the container and the outside atmosphere under steady state conditions can be limited by suitably reducing the diameter of the gas conduit (also known as "vent tube") and/or by increasing its length. Thus, in general, with a gas conduit of relatively small diameter and relatively long length, said gaseous exchange can be substantially avoided for a relatively long period of time. However, the Applicant has also observed that if the diameter of the gas conduit is too small and/or its length is too long, the pressure inside the container can reach excessively high (or low) values during injection (or withdrawal, respectively) of a (quick) liquid into the container, which can be undesirable for the user and may negatively affect the content of container (e.g. in the case of suspensions of gas-filled microvesicles). The gas conduit of a liquid transfer device according to the invention is thus preferably dimensioned so as to avoid differential pressure of more than about 300 mbar, preferably of more 200 mbar and even more preferably of more than 100 mbar between the container and the external ambient upon injection or withdrawal of a liquid therein.

In the practice, for maintaining said gas exchange below said values in steady state conditions, it has been observed that the mean diameter of the gas conduit shall preferably be lower than about 0.7 mm, more preferably lower than about 0.5 mm and even more preferably lower than about 0.4 mm. To avoid the creation of the above cited differential pressures between the container and the external ambient, conduits with a diameter of at least 0.1 mm or larger are preferably selected, more preferably with a diameter of at least 0.2 mm or larger. For the sake of clarity, in the present description and claims, the term "diameter" of a gas conduit refers either to the effective diameter in the case of a conduit having a substantially constant section or to the mean diameter of the conduit in the case of conduits having a variable section. Thus, for instance, for a conduit having a total length of 100 mm, 10 mm of which have a diameter of 0.1 mm and 90 mm of which have a diameter of 0.5 mm, the (mean) diameter of the conduit will be of 0.46 mm.

The length of the gas conduit is adapted to the corresponding diameter of the conduit, taking into account the opposite requirements of limiting the gas exchange (for which longer lengths are preferred) and of avoiding the creation of an excessive differential of pressure between the container and the outside atmosphere (for which shorter lengths are preferred). In general, to take into account the above opposite requirements, shorter conduit's lengths are preferably associated with smaller diameters, while longer lengths can be associated with larger diameters. The length of the gas conduit is preferably from about 2.5 mm to about 400 mm, more preferably from about 5 mm to about 250 mm and even more preferably from about 10 mm to about 150 mm. As a general guidance, the ratio between the length of the gas conduit and its diameter is comprised between 25 and 600, preferably between 50 and 500 and more preferably between 150 and 400.

The above dimensions of the gas conduit are particularly suitable when the volume of gas in the container is of at least 2 ml, preferably from about 2 to about 20 ml. For larger volumes of gas, the mean diameter of the conduit can in general be increased accordingly, as the same absolute amount of gas exchanged in the unit of time will represent a lower volume percentage of the total (larger) volume.

Figure 7:
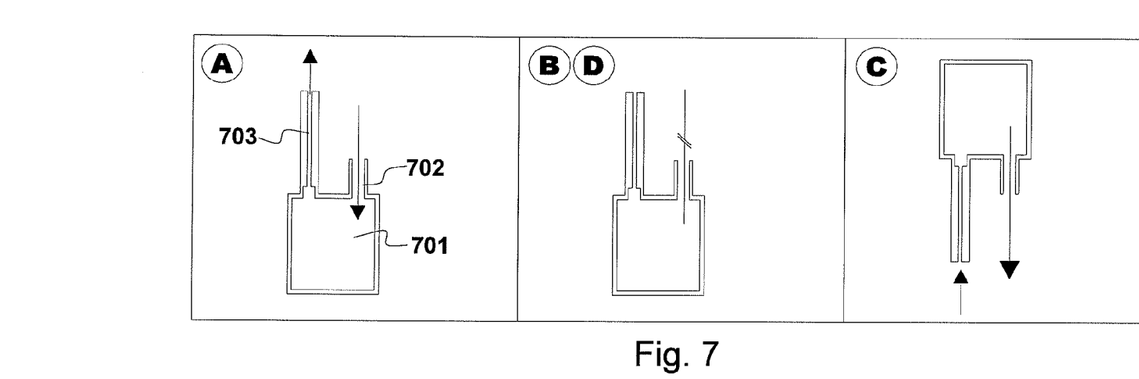
FIG. 7 schematically illustrates the phases involved in the preparation of a medicament with a liquid transfer device according to the invention.
Figure 8:
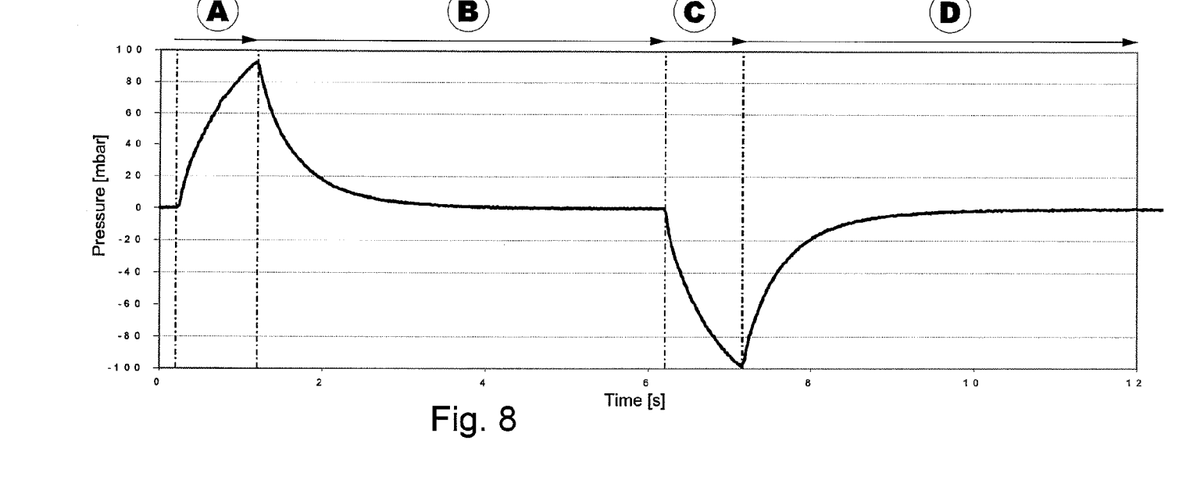
FIG. 8 shows the corresponding pressure diagram of the preparation steps A to D illustrated in FIG. 7.

FIG. 7 schematically illustrates the steps involved in the preparation of a pharmaceutically active formulation by using a transfer device according to the invention. The transfer device is used for injecting a physiologically acceptable liquid carrier into a vial containing a precursor of a pharmaceutically active formulation for reconstitution thereof (the total volume of the vial is e.g. of about 10 ml). The pharmaceutically active formulation can be for instance a suspension of gas-filled microvesicles which is reconstituted from a dry powder (e.g. comprising a phospholipid) deposited on the bottom of the vial, in an atmosphere of a physiologically acceptable gas (e.g. sulfur hexafluoride or perfluorobutane). The assembly of the vial and of the transfer device is schematically depicted as a box 701, connected to a first conduit 702, for the injection/withdrawal of the liquid, and to a second conduit 703 for the gas flow. FIG. 8 shows a schematic pressure diagram illustrating the variation of pressure occurring during the steps A to D of FIG. 7.

In particular, when a forward flow is caused by a quick injection (e.g. at a flow rate of about 2 ml/s) of a liquid carrier into the vial 701 (step A), the pressure inside the container suddenly increases up to a certain value (e.g. about 100 mbar in FIG. 8), said pressure increase depending mainly from the injection's speed and from the dimensions of the ventilation conduit (in particular its diameter). When the injection of liquid is terminated, conduit 702 is sealed (e.g. by leaving the syringe in place) and the internal pressure decreases down to the pressure of the external ambient (step B). To withdraw the liquid (e.g. in the form of a reconstituted suspension) from the vial, the vial is turned upside-down. When the liquid is then withdrawn (step C) from the vial, the internal pressure inside the vial decreases down to a minimum. At the end of the liquid withdrawal (step D), the internal pressure then increases again, to equalize the value of the ambient pressure.

Figure 1:
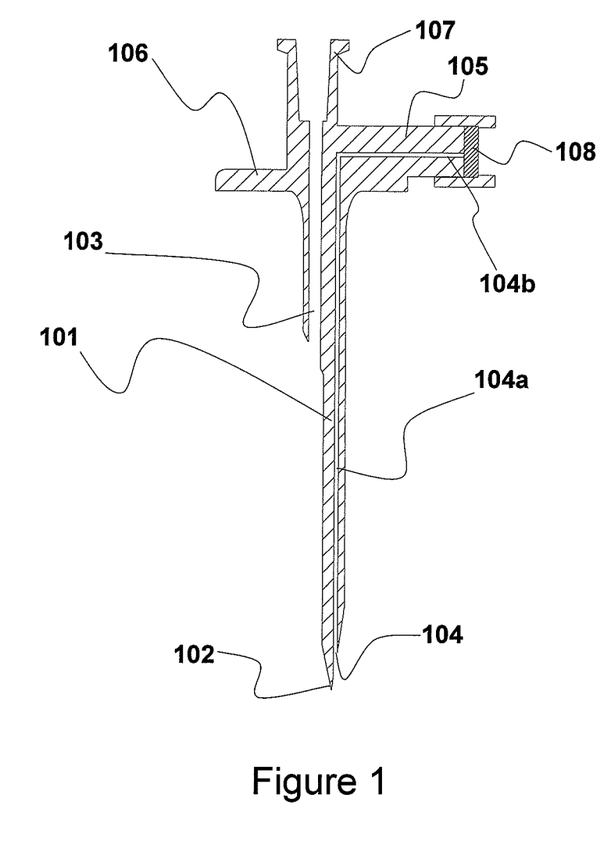
FIGS. 1-3 show cross sectional views of three different embodiments of a liquid transfer device according to the invention.

With reference to FIG. 1, a first embodiment of a liquid transfer device according to the invention is shown. The liquid transfer device comprises a spike 101 having a sharp end 102 for piercing the closure of a dispensing container, a liquid fluid passage 103 and a gas passage 104 opening at a tip. The spike 101, formed as an integral member with the fluid passage 103 and the gas passage 104, carries an upper body member 105 that includes a handle 106. The fluid passage 103 extends substantially parallel to the longitudinal axis of the spike 101 throughout its length and ends into a connecting piece 107 (e.g. a luer connector) for connecting the transfer device with an external device (not shown), e.g. a syringe. The gas passage 104 extends parallelly to the fluid passage 103 through the spike 101 and the body member 105 for its first portion 104a, while its final portion 104b it extends radially outwardly with respect to the spike axis. An optional hydrophobic filter 108 is preferably provided at the end of the gas passage, for protecting the content of the vial against possible microbial contamination (e.g. with the air-inlet during liquid withdrawal). The filter is preferably adapted to avoid undesirable liquid leakage outside the vial, e.g. when the device-vial assembly is turned upside down for liquid removal. The hydrophobic filter has typical pore sizes of from about 0.20 µm to about 0.50 µm.

Figure 2:
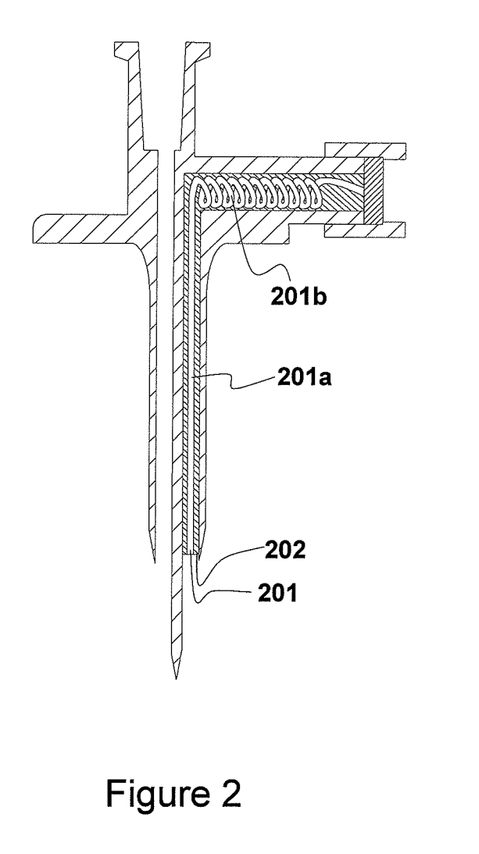

FIG. 2 shows an alternative embodiment of a liquid transfer device according to the invention. In this embodiment, the gas passage is formed by a conduit 201 disposed inside a larger tubular seat 202; the tubular seat 202 is filled with a sealing material, for instance a resin (e.g. a composite resin), to seal the seat and fix the conduit 201 therein. According to this embodiment, the portion 201a of the conduit extending parallel to axis of the spike can advantageously be shortened, said reduction being compensated by the increased length of the radially extending portion 201b in spiral form. The length of the conduit for the gas passage can suitably be adapted to any specific need, by varying the number of turns in the spiral-form portion 201b of the conduit.

Figures 3, 4:
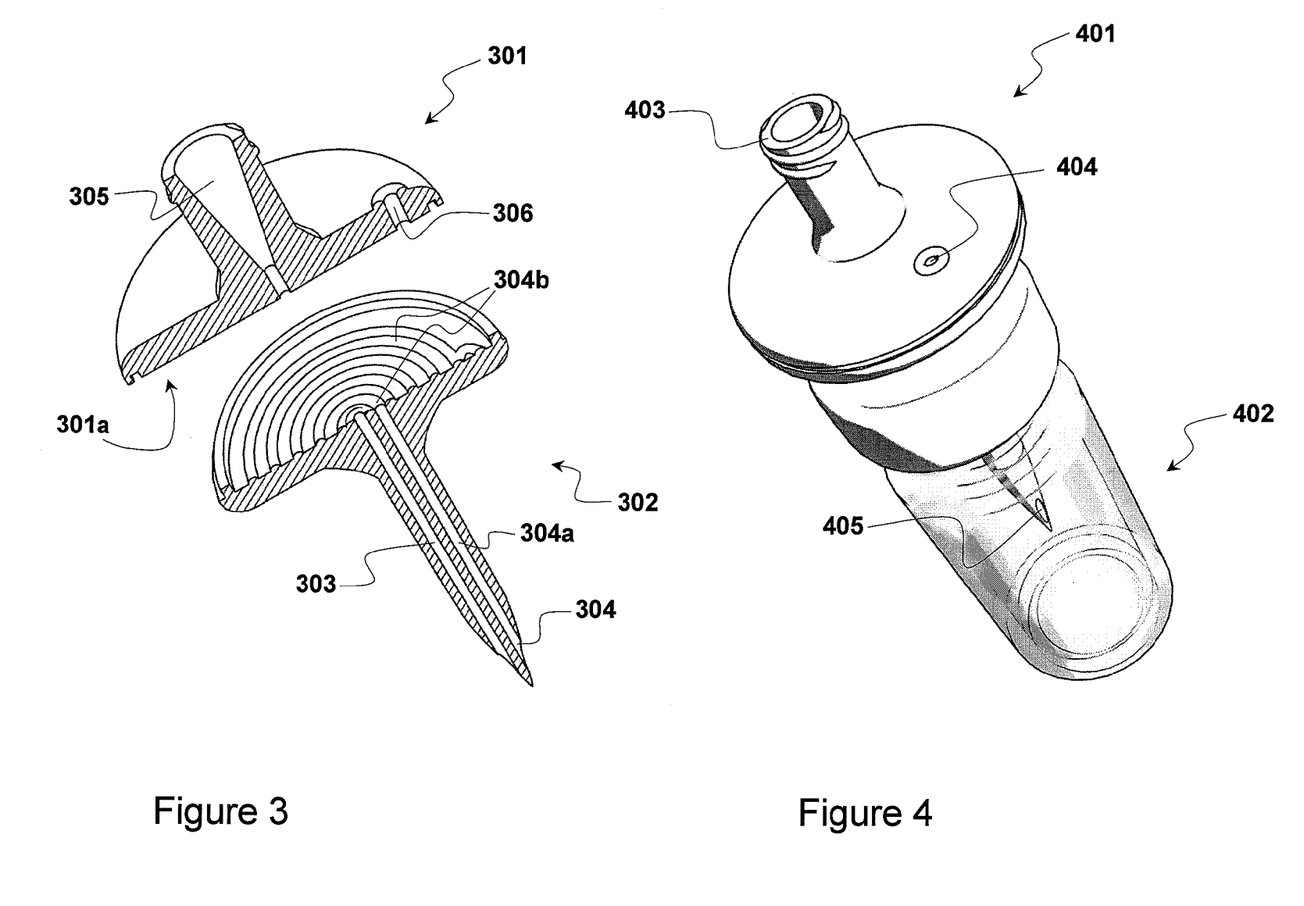
FIG. 4 shows a liquid transfer according to FIG. 3 cooperating with a medical dispensing container.

FIG. 3 shows a further embodiment of a liquid transfer device according to the invention, where the length of the portion of the gas passage extending parallelly to the axis of the spike can advantageously be shortened. As shown in FIG. 3, the device preferably comprises an upper part 301 and a lower part 302. The lower part 302 comprises a liquid passage 303 and a gas passage 304, disposed parallelly to the spike's longitudinal axis. The liquid passage ends in the upper part 301 of the device, into a connecting piece 305 (e.g. a luer connector) for connecting the transfer device with an external device (not shown), e.g. a syringe. The connecting piece 305 can advantageously be provided with means for closing the liquid conduit (not shown) when the device is not connected to a syringe. Examples of means for closing said liquid conduit include, for instance, a self-closing valve (such as the one disclosed in U.S. Pat. No. 6,743,214, herein incorporated by reference) and/or a removable cap (e.g. as disclosed in the above cited U.S. Pat. No. 6,743,214). The gas passage 304 comprises a lower portion 304a disposed parallelly to the axis of the spike. This lower portion is connected to a spiroidal-path portion 304b, disposed into the upper portion of the lower part 302 of the device. The spiroidal path 304b ends into a gas vent 306, communicating with the external ambient. The gas vent can optionally comprise a hydrophobic filter, such as the one described in connection with FIG. 1. The bottom portion 301a of the upper part 301 can either be flat as shown if FIG. 3 or can be provided with a spiroidal path specular with respect to the spiroidal path 304a and thus matching therewith (not shown); whichever the case, the cooperation of the bottom and of the upper part form a continuous gas conduit from the bottom portion of the spike until the gas vent 306. According to this embodiment, the length of the gas passage can advantageously be adapted to the specific needs, by acting on the length of the spiroidal path, without modifying the length of the portion parallel to the axis of the device.

Any of the above described transfer devices can be used in combination with a vial containing a gas, for the injection of a liquid into said vial and for controlling the gas exchange between the container and the external ambient under steady state conditions.

For instance, FIG. 4 shows an assembly comprising a liquid transfer device 401 according to FIG. 3 which cooperates with a glass vial 402, containing e.g. a physiologically acceptable gas and a lyophilized residue (not shown). The transfer device is in turn connected through the connecting portion 403 with a syringe (not shown), containing the liquid for reconstituting the lyophilized residue (e.g. as a suspension of gas-filled microvesicles). The glass vial is typically provided with a rubber stopper (not shown), which is pierced by the spike of the transfer device connected to a pre-filled syringe, to allow the liquid transfer into and from the vial. The upper portion of the transfer device comprises the gas vent 404, connected through a spiral path (not shown) to the entry of the gas passage 405 at the bottom end of the spike.

Figure 5:
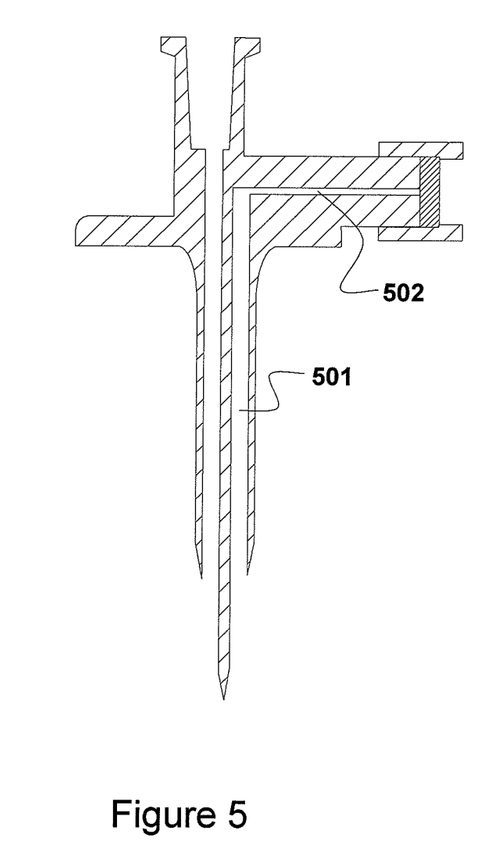
FIGS. 5-6 show cross sectional views of two further embodiments of a liquid transfer device according to the invention.
Figure 6:
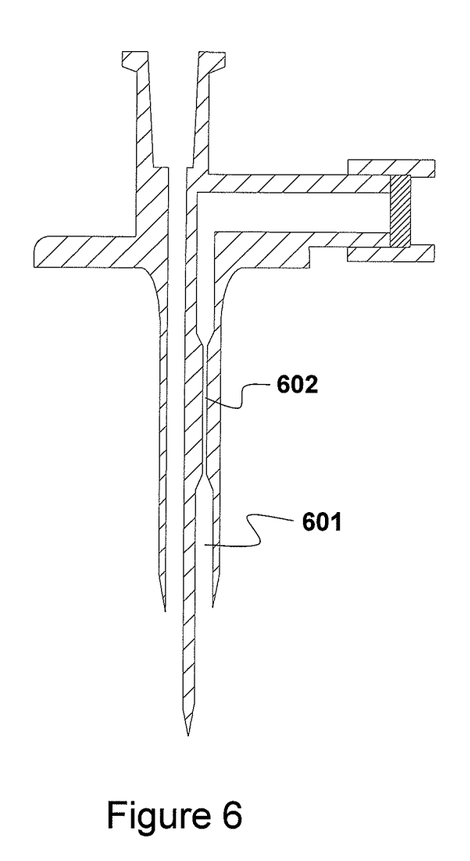

FIGS. 5 and 6 show alternative embodiments of a liquid transfer device according to the invention, where the section (or diameter) of the gas conduit is not constant. As it can be appreciated by those skilled in the art, the presence of suitable restrictions 502 and 602 in the respective gas conduits 501 and 601 allows to accordingly reduce the length of the conduits.

As mentioned before, the transfer device of the invention can advantageously be used for injecting/withdrawing a liquid into/from a container which contains a pharmaceutically active formulation comprising a gaseous material. The use of the transfer device is particularly advantageous when the gaseous material is a diagnostically and/or therapeutically effective agent, such as gaseous materials employed for the preparation of gas-filled microvesicles for use in ultrasound diagnostic and/or therapeutic methods.

The term "pharmaceutically active formulation" includes within its meaning any formulation, or precursor thereof, capable of exerting a pharmaceutical effect when administered in an effective amount, including diagnostic and/or therapeutic effects. Examples of pharmaceutically active formulations are those formulations which comprise, for instance, a diagnostic agent and/or a bioactive agent.

The term "diagnostic agent" includes within its meaning any compound, composition or particle which may be used in connection with methods for imaging an internal region of a patient and/or diagnosing the presence or absence of a disease in a patient. Exemplary diagnostic agents include, for example, contrast agents for use in connection with ultrasound, magnetic resonance imaging, X-ray imaging, in particular computed tomography, optical imaging, nuclear imaging or molecular imaging of a patient including, for example, magnetite nanoparticles.

The term "bioactive agent" includes within its meaning any substance, composition or particle which may be used in any therapeutic application, such as in methods for the treatment of a disease in a patient, as well as any substance which is capable of exerting or responsible to exert a biological effect in vitro and/or in vivo. Examples of bioactive agents are drugs, medicaments, pharmaceuticals, proteins, natural or synthetic peptides, including oligopeptides and polypeptides, vitamins, steroids and genetic material, including nucleosides, nucleotides and polynucleotides.

In particular, said container can be a vial (e.g. of glass) containing a suspension of gas-filled microvesicles, such as those disclosed in the above mentioned documents, U.S. Pat. No. 5,271,928, U.S. Pat. No. 5,445,813, U.S. Pat. No. 5,413,774, U.S. Pat. Nos. 5,556,610, 5,597,549, U.S. Pat. No. 5,827,504, WO 97/29783, WO 04/069284, U.S. Pat. No. 5,711,933 and U.S. Pat. No. 6,333,021, all herein incorporated by reference. According to a preferred embodiment, said vial comprises a precursor of said microvesicles in the form of a dry powdered deposit in contact with a physiologically acceptable gas. Preferably the microvesicles, or their precursor, are gas-filled microbubbles stabilized by a layer of amphiphilic material. Preferably said amphiphilic material comprises a phospholipid, such as fatty acids di-esters of phosphatidylcholine, ethylphosphatidylcholine, phosphatidylglycerol, phosphatidic acid, phosphatidyl-ethanolamine, phosphatidylserine, sphingomyelin or mixtures thereof. Examples of preferred phospholipids are, for instance, dilauroyl-phosphatidylcholine (DLPC), dimyristoyl-phosphatidylcholine (DMPC), dipalmitoyl-phosphatidylcholine (DPPC), diarachidoyl-phosphatidylcholine (DAPC), distearoyl-phosphatidylcholine (DSPC), dioleoyl-phosphatidylcholine (DOPC), 1,2 Distearoyl-sn-glycero-3-Ethylphosphocholine (Ethyl-DSPC), dipentadecanoyl-phosphatidylcholine (DPDPC), 1-myristoyl-2-palmitoyl-phosphatidylcholine (MPPC), 1-palmitoyl-2-myristoyl-phosphatidylcholine (PMPC), 1-palmitoyl-2-stearoyl-phosphatidylcholine (PSPC), 1-stearoyl-2-palmitoylphosphatidylcholine (SPPC), 1-palmitoyl-2-oleylphosphatidylcholine (POPC), 1-oleyl-2-palmitoyl-phosphatidylcholine (OPPC), dilauroyl-phosphatidylglycerol (DLPG) and its alkali metal salts, diarachidoylphosphatidyl-glycerol (DAPG) and its alkali metal salts, dimyristoylphosphatidylglycerol (DMPG) and its alkali metal salts, dipalmitoylphosphatidylglycerol (DPPG) and its alkali metal salts, distearoylphosphatidylglycerol (DSPG) and its alkali metal salts, dioleoyl-phosphatidylglycerol (DOPG) and its alkali metal salts, dimyristoyl phosphatidic acid (DMPA) and its alkali metal salts, dipalmitoyl phosphatidic acid (DPPA) and its alkali metal salts, distearoyl phosphatidic acid (DSPA), diarachidoylphosphatidic acid (DAPA) and its alkali metal salts, dimyristoyl-phosphatidylethanolamine (DMPE), dipalmitoylphosphatidylethanolamine (DPPE), distearoyl phosphatidyl-ethanolamine (DSPE), dioleylphosphatidyl-ethanolamine (DOPE), diarachidoylphosphatidyl-ethanolamine (DAPE), dilinoleylphosphatidylethanolamine (DLPE), dimyristoyl phosphatidylserine (DMPS), diarachidoyl phosphatidylserine (DAPS), dipalmitoyl phosphatidylserine (DPPS), distearoylphosphatidylserine (DSPS), dioleoylphosphatidylserine (DOPS), dipalmitoyl sphingomyelin (DPSP), and distearoylsphingomyelin (DSSP).

The term phospholipid further includes modified phospholipid, e.g. phospholipids where the hydrophilic group is in turn bound to another hydrophilic group. Examples of modified phospholipids are phosphatidylethanolamines modified with polyethylenglycol (PEG), i.e. phosphatidylethanolamines where the hydrophilic ethanolamine moiety is linked to a PEG molecule of variable molecular weight e.g. from 300 to 5000 daltons), such as DPPE-PEG or DSPE-PEG, i.e. DPPE (or DSPE) having a PEG polymer attached thereto. For example, DPPE-PEG2000 refers to DPPE having attached thereto a PEG polymer having a mean average molecular weight of about 2000.

The phospholipids can optionally be admixed with other lipids, such as cholesterol, ergosterol, phytosterol, sitosterol, lanosterol, tocopherol, propyl gallate or ascorbyl palmitate, fatty acids such as myristic acid, palmitic acid, stearic acid, arachidic acid and derivatives thereof.

Bulking agents, having cryoprotective and/or lyoprotective effects, can also be added to the composition, such as, for instance, an amino-acid such as glycine; a carbohydrate, e.g. a sugar such as sucrose, mannitol, maltose, trehalose, glucose, lactose or a cyclodextrin, or a polysaccharide such as dextran; or a polyglycol such as polyethylene glycol.

Any biocompatible gas, gas precursor or mixture thereof may be employed to fill the above microvesicles.

In the present description and claims, the term "biocompatible" or "physiologically acceptable" refers to any compound, material or formulation (in solid, liquid or gaseous form) which can be administered, in a selected amount, to a patient without negatively affecting or substantially modifying its organism's healthy or normal functioning (e.g. without determining any status of unacceptable toxicity, causing any extreme or uncontrollable allergenic response or determining any abnormal pathological condition or disease status).

Suitable gases may comprise, for example nitrogen; oxygen; carbon dioxide; hydrogen; nitrous oxide; a noble or inert gas such as helium, argon, xenon or krypton; a radioactive gas such as $Xe^{133}$ or $Kr^{81}$; a hyperpolarized noble gas such as hyperpolarized helium, hyperpolarized xenon or hyperpolarized neon; a low molecular weight hydrocarbon (e.g. containing up to 7 carbon atoms), for example an alkane such as methane, ethane, propane, butane, isobutane, pentane or isopentane, a cycloalkane such as cyclobutane or cyclopentane, an alkene such as propene, butene or isobutene, or an alkyne such as acetylene; an ether; a ketone; an ester; halogenated gases, preferably fluorinated gases, such as or halogenated, fluorinated or perfluorinated low molecular weight hydrocarbons (e.g. containing up to 7 carbon atoms); or a mixture of any of the foregoing. Where a halogenated hydrocarbon is used, preferably at least some, more preferably all, of the halogen atoms in said compound are fluorine atoms.

Fluorinated gases are preferred, in particular perfluorinated gases, especially in the field of ultrasound imaging. Preferred compounds are perfluorinated gases, such as $SF_6$ or perfluorocarbons (perfluorinated hydrocarbons), i.e. hydrocarbons where all the hydrogen atoms are replaced by fluorine atoms. The term perfluorocarbon includes saturated, unsaturated, and cyclic perfluorocarbons. Suitable perfluorocarbons include, for example, $CF_4$, $C_2F_6$, $C_3F_8$, $C_4F_8$, $C_4F_{10}$, $C_5F_{12}$, $C_6F_{12}$, $C_6F_{14}$, $C_7F_{14}$, $C_7F_{16}$, $C_8F_{18}$, and $C_9F_{20}$; preferably $C_3F_8$, $C_4F_{10}$ or $C_5F_{12}$ are employed, optionally in admixture with air or nitrogen.

The gas is typically introduced in the container containing the lyophilized precursor of microvesicles at about atmospheric pressure (i.e. about 1020 mbar+/−5%) or at a pressure lower than the atmospheric one (e.g. 900 mbar or lower) as disclosed e.g. in European patent application EP 1228770. The container is then typically sealed by a gas-seal stopper, preferably made from an elastomeric compound or multi-component formulation based on an elastomer, such as poly (isobutylene) or butyl rubber. Conveniently, a butyl rubber stopper (e.g. from Daikyo Seiko ltd., Japan) can be used.

Microvesicles suspensions are then formed by introduction of a suitable physiologically acceptable liquid carrier into the container followed by agitation of the mixture to reconstitute an injectable composition. The gas contained in the microvesicles thus acts as a pharmaceutically active component of the composition, in particular as a diagnostically active component.

Suitable physiologically acceptable liquid carriers are sterile water, aqueous solutions such as saline (which may advantageously be balanced so that the final product for injection is not hypotonic), or solutions of one or more tonicity adjusting substances such as salts or sugars, sugar alcohols, glycols or other non-ionic polyol materials (eg. glucose, sucrose, sorbitol, mannitol, glycerol, polyethylene glycols, propylene glycols and the like).

The liquid transfer device as above defined can advantageously be included in a kit comprising said device and a container containing a pharmaceutically active formulation comprising a gaseous material as a pharmaceutically active component thereof. The kit typically further comprises a physiologically acceptable liquid carrier, for reconstituting the suspension of gas-filled microvesicles. The liquid carrier is preferably contained into a separate container (typically in the form of a syringe) which is used for injecting the liquid carrier into the container and for withdrawing the reconstituted suspension therefrom, through the liquid transfer device. Although in general hand shaking of the container provides the desired energy for reconstituting the suspension, means for directing or permitting application of sufficient energy towards the container can also be provided (e.g. a Vortex mixer), in order to assure suitable reconstitution of the suspension.

The liquid transfer device as above defined can thus be used for reconstituting a suspension of gas-filled microvesicles, by connecting a syringe to the liquid transfer device, introducing the physiologically acceptable liquid of the syringe into the vial containing the dry powdered precursor of said gas-filled microbubbles (in contact with the desired gas), agitating the content of the vial and withdrawing the obtained suspension.

Due to the improved characteristics of the liquid transfer device, the phase of removal of the suspension can be performed several hours or days after the reconstitution of the pharmaceutically active formulation, without substantially altering the content of gas/air of the reconstituted formulation.

EXAMPLES

Example 1

Measure of Gas Exchange with Different Valves 150 vials (each having an internal volume of about 11 $cm^3$) are filled with $SF_6$ gas at room temperature up to about atmospheric pressure and sealed with a rubber stopper.

The vials are divided in fifty groups of three vials each and the stopper of each vial is then pierced with a liquid transfer device as indicated hereinafter.

Device D1 (comparative) is a commercial Mini-Spike® Dispensing Pin DP-1000 (B. Braun Melsungen AG, Melsungen DE).

This device corresponds to the device of FIG. 2, where the tubular seat 202 is devoid of resin and of gas conduit 201. The tubular seat 202 is thus a gas passage with a first portion (parallel to the spike's axis) of 17 mm length and 1.10 mm diameter, and a second portion (extending radially outwardly from the spike's axis) of 11 mm length and 4.25 mm diameter, for a total length of 28 mm and a mean diameter of 2.3 mm.

The other liquid transfer devices of the example (D2-D10) have been obtained by inserting various polymeric tubes of different diameters (0.17, 0.28 and 0.58 mm) and different lengths (2.5, 5 and 10 cm) into the tubular passage of the above Mini-Spike® Dispensing Pin and sealing the passage with a resin (Agovit® 1900 with Katalysor 20, Degussa AG, Düsseldorf, DE). For the 0.17 mm diameter tube, a PEEK capillary (Fischer Scientific SA, Wohlen, CH) has been used; for the 0.28 and 0.58 mm diameter tube, a polythene tubing (Sims Portex Ltd, Hythe, UK) has been used. A total of 9 devices has been used, with the following dimensions of gas conduit:

Device D2: diameter 0.17; length 2.5 cm.
Device D3: diameter 0.17; length 5.0 cm.
Device D4: diameter 0.17; length 10 cm.
Device D5: diameter 0.28; length 2.5 cm.
Device D6: diameter 0.28; length 5.0 cm.
Device D7: diameter 0.28; length 10 cm.
Device D8: diameter 0.58; length 2.5 cm.
Device D9: diameter 0.58; length 5.0 cm.
Device D10: diameter 0.58; length 10 cm.

Groups of three devices of each type are used for piercing respective groups of three vials. The three vials of each group are used to determine the mean content of air penetrated therein as a function of time, by removing the devices from the vials after 0, 30, 60, 180 and 360 minutes, respectively, sealing the vial and measuring the residual concentration of $SF_6$ by means of gas-chromatograph GC 6890 Hewlett-Packard Co., Wilmington, USA, equipped with a Headspace injector Hewlett-Packard Co., Wilmington, USA and TCD detector (capillary column: Chrompack plot Fused silica 25 m×0.32 mm coating Poraplot Q, Chrompack International BV, Bergen, NL).

Figure 9:
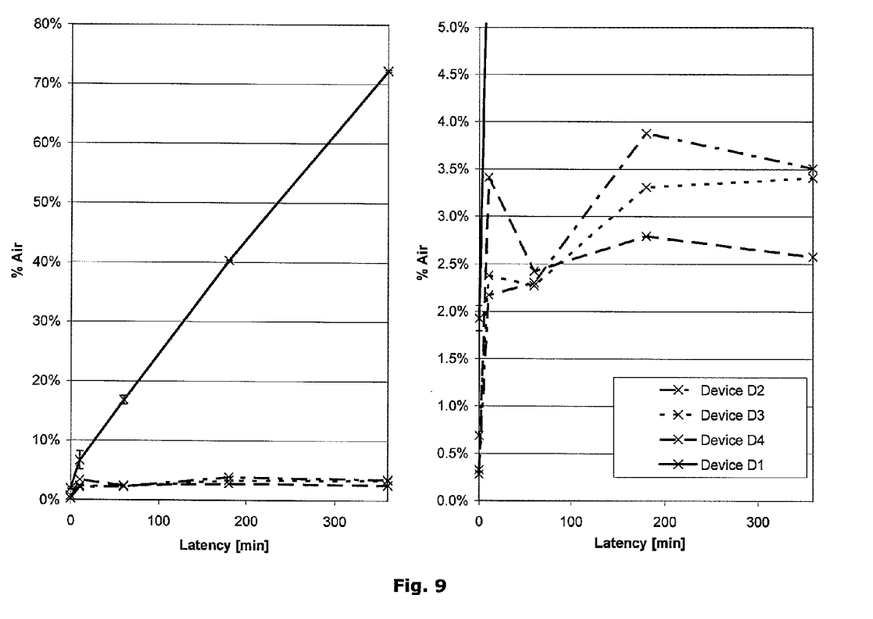
FIGS. 9 to 11 show the diagram of air diffusion as a function of time, measured for different liquid transfer devices.
Figure 10:
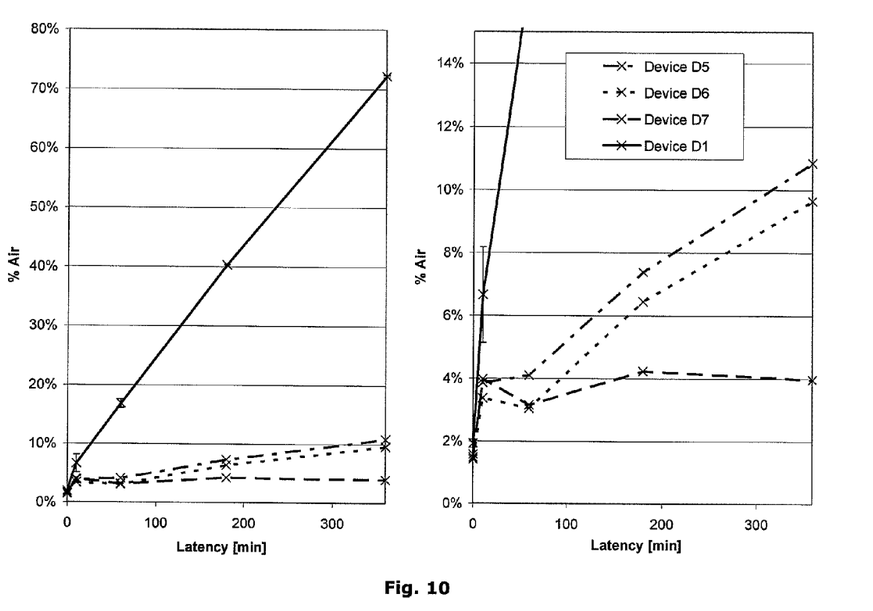
Figure 11:
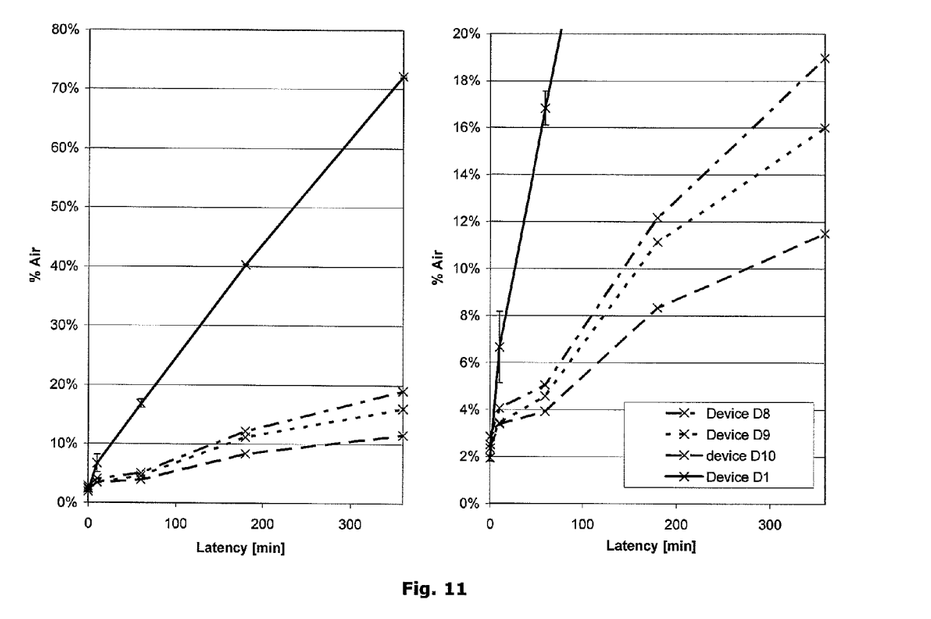

The difference to 100% gives the amount of air penetrated in the vial. FIGS. 9 to 11 show the results of the experiments, indicating that the modification of vent design (internal diameter and length) in transfer device allows to substantially limit the penetration of air inside the vial with respect to a device with a conventional vent.

Example 2

Measure of Injection Overpressure

To measure the pressure variation inside a vial upon liquid injection by using transfer devices D2-D10 according to example 1, the following set-up has been used.

Figure 12:
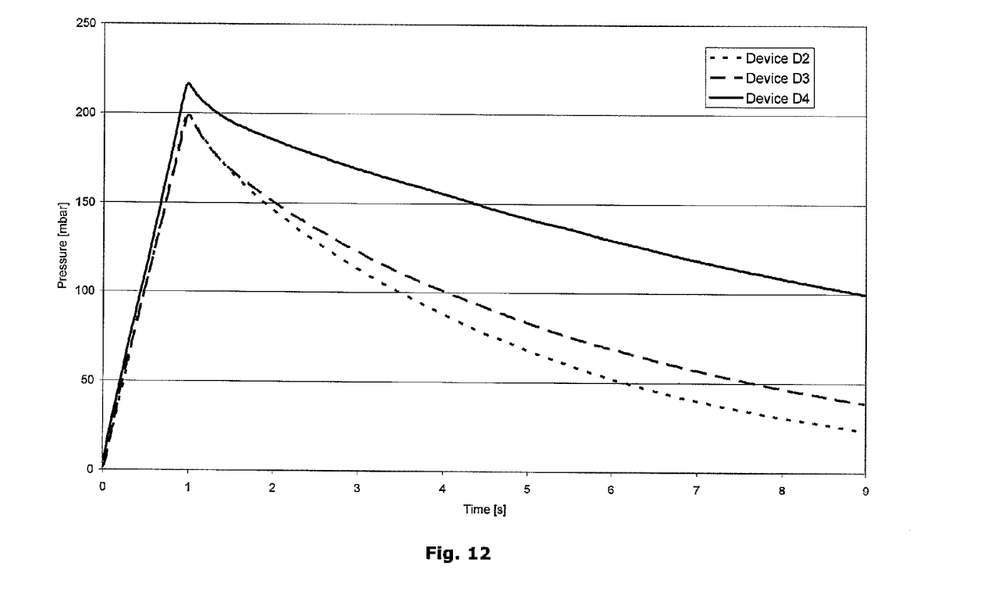
FIGS. 12 to 14 show the pressure diagram associated with a liquid injection and withdrawal by using various transfer devices of the invention.
Figure 13:
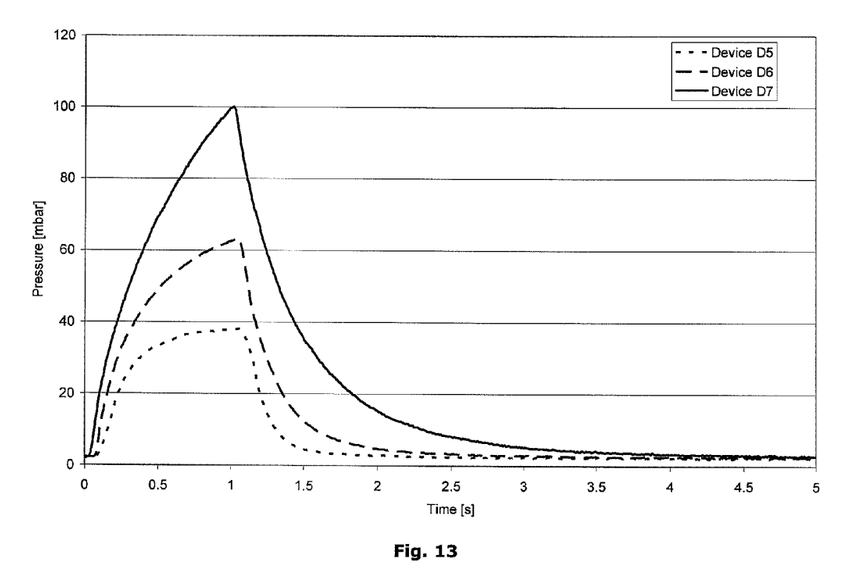
Figure 14:
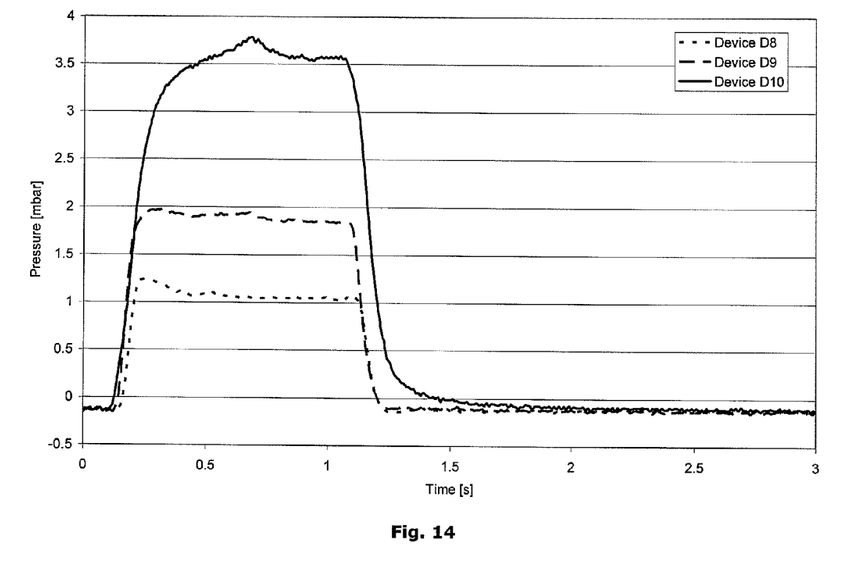

A calibrated differential pressure transducer (COBE® pressure sensor Ref: #041-500-5003, COBE, Lakewood, USA) is attached to a 20 G1½ needle and then inserted in a vial by piercing of rubber stopper. A syringe filled with 2 ml of saline solution is attached to the liquid conduit of the device of example 1, and then inserted in the vial as described in example 1. The syringe plunger is moved at constant speed to allow a substantially constant injection rate (2 ml/s) in the vial, for a total volume of 2 ml. FIGS. 10 to 12 show the variation of pressure inside the vial as a function of time, for the different liquid transfer devices D2 to D10. As it can be appreciated by the figures, higher overpressures are attained with devices having smaller diameters and longer lengths.

Example 3

Measure of Gas Exchange with Device with Alternate Vent Tube 6 vials (each with internal volume of about 11 $cm^3$) are filled with $SF_6$ gas at room temperature up to about atmospheric pressure and sealed with a rubber stopper.

The vials are divided in two groups of three vials each and the stopper of each vial is then pierced with a liquid transfer device as indicated hereinafter:

Device D1 as above defined;
Device D11: according to the device of FIG. 2, derived from device D1 by inserting a gas conduit of 0.17 diameter and 0.5 mm length into the outwardly radially extending portion of the gas conduit of D1.

The analytical operating procedure is the same as described in the example 1. The efficiency of gas exchange is measured after 360 minutes. Table 1 shows the results of the experiment, indicating that the modification of vent design in transfer device allow to substantially limit the penetration of air inside the vial with respect to a device with a normal vent.

TABLE 1

| Device | % Air after 360 min of latency |
|---|---|
| D1 | 72% |
| D11 | 8% |

Measure of Injection Overpressure

Figure 15:
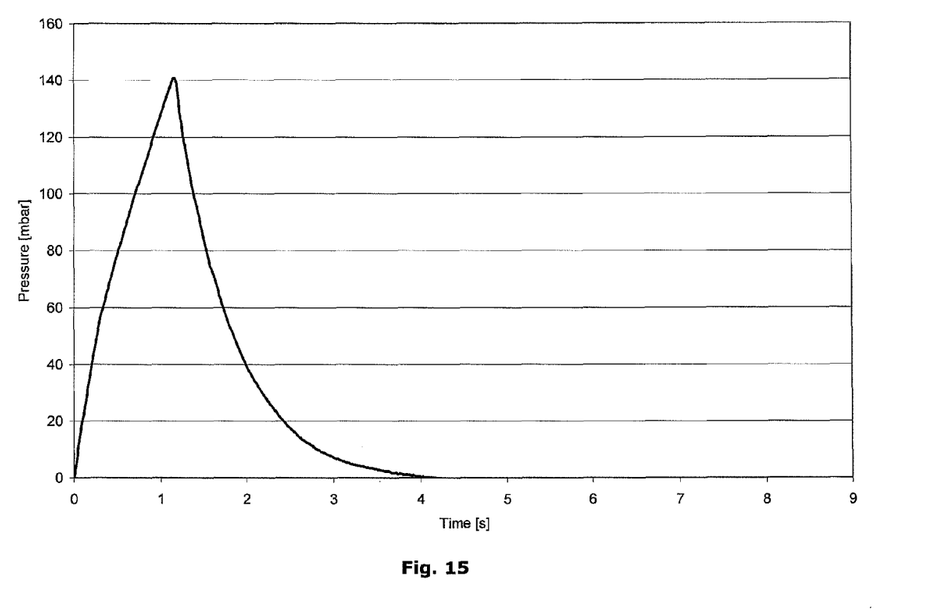
FIG. 15 shows the pressure diagram associated with a liquid injection and withdrawal by using a further transfer device of the invention.

The operating procedure according to example 2 is applied on device with vent tube of example 3. FIG. 15 shows the variation of pressure inside the vial as a function of time.

Example 4

Measure of Gas Exchange with Alternate Gas and Different Tubing Spike Vent 12 vials (each having an internal volume of about 11 $cm^3$) are filled with $C_4F_{10}$ gas at room temperature up to about atmospheric pressure and sealed with a rubber stopper. The vials are divided in four groups of three vials each and the stopper of each vial is then pierced with respective groups of three of the following liquid transfer devices: Device D1, Device D5, Device D6 and Device D7.

The analytical operating procedure is the same as described in the example 1. The efficiency of gas exchange is measured after 180 min.

Table 2 shows the results of the experiments, indicating that the modification of vent design in transfer device allows to substantially limit the penetration of air inside the vial with respect to a device with a conventional vent.

TABLE 2

| Device | % Air after 180 min of latency |
|--------|-------------------------------|
| D1 | 31% |
| D5 | 5% |
| D6 | 5% |
| D7 | 2% |

The invention claimed is:

1. Pharmaceutical kit for the preparation of a medicament comprising:
    a) a medical dispensing container defining an inner space and containing a physiologically acceptable gas therein, and
    b) a liquid transfer device, which cooperates with said container for transferring a liquid into or from said container, said device comprising a first conduit and a second conduit said first and said second conduit allowing a fluid contact between the inner space and an external ambient when said device cooperates with said container, wherein:
        said second conduit has (i) a first portion which is substantially parallel to said first conduit and (ii) a second portion which has a plurality of turns around an axis and is in communication with said external ambient;
        when said device cooperates with the container during a liquid flow into or from said dispensing container, said liquid flow is effected through said first conduit while said second conduit allows a free gaseous flow between said container and an external ambient; and
        when said device cooperates with the container in steady state conditions, less than 20% (v/v) of the total volume of gas contained in said container is exchanged with the external ambient over a period of 6 hours;
        said second conduit having a length (l) and a diameter (d) such that the ratio l/d is between about 86 and about 600 and being substantially devoid of means for interrupting the flow of gas between said container and the external ambient.

2. A kit according to claim 1, wherein said container further contains a precursor of a suspension of gas-filled microvesicles in the form of a dry deposit.

3. A kit according to claim 1, wherein less than 10% (v/v) of said gas is exchanged.

4. A kit according to claim 1, wherein less than 5% v/v of said gas is exchanged.

5. A kit according to claim 1, wherein, when said transfer device cooperates with the container during a liquid flow into or from said container, said inner space of the container is subjected to a differential pressure with respect to the external ambient of less than about 300 mbar.

6. A kit according to claim 5 wherein said differential pressure is less than 200 mbar.

7. A kit according to claim 5, wherein said differential pressure is less than 100 bar.

8. A kit according to any one of claim 1, 2 or 5, wherein said second conduit comprises filtering means for protecting the content of the container against microbial contamination during liquid withdrawal.

9. A kit according to claim 8, wherein said filtering means comprise a hydrophobic filter.

10. A kit according to any one of claim 1, 2 or 5, wherein said first conduit of the transfer device comprises connecting means for connecting the transfer device with an external device containing the liquid to be transferred.

11. A kit according to claim 10, characterized in that said connecting means comprise a luer connector.

12. A kit according to any one of claims 1 or 5, wherein said second conduit of said transfer device has a diameter of less than 0.7 mm.

13. A kit according claim 12, wherein said diameter is less than 0.5 mm.

14. A kit according claim 12, wherein said diameter is less than 0.4 mm.

15. A kit according to any one of claim 1 or 5, wherein said second conduit of said transfer device has a length of from about 2.5 mm to about 400 mm.

16. A kit according to claim 15, wherein said length is from about 5 mm to about 250 mm.

17. A kit according to claim 15, wherein said length is from about 10 mm to about 150 mm.

18. A kit according to claim 1, wherein said ratio lid is between 86 and 500.

19. A kit according to claim 18, wherein said ratio lid is between 150 and 400.

20. A kit according to any one of claim 1 or 5, wherein said first conduit comprises shutter means for closing said conduit when a fluid injector is removed.

21. A kit according to any one of claim 1 or 2, further comprising a syringe pre-filled with a saline solution.

22. A kit according to any one of claim 1 or 2, wherein said physiologically acceptable gas is a diagnostically and/or therapeutically effective agent.

* * * * *

UNITED STATES PATENT AND TRADEMARK OFFICE
CERTIFICATE OF CORRECTION

PATENT NO.         : 9,238,103 B2
APPLICATION NO.    : 12/086310
DATED              : January 19, 2016
INVENTOR(S)        : Laurent Jakob et al.

It is certified that error appears in the above-identified patent and that said Letters Patent is hereby corrected as shown below:

IN THE CLAIMS

Column 14, line 6, cancel the text beginning with "4. A kit according" to and ending with "gas is exchanged." in column 14, line 7, and insert the following claim:

--4. A kit according to claim 1, wherein less than 5% (v/v) of said gas is exchanged.--

Column 14, line 15, cancel the text beginning with "7. A kit according" to and ending with "100 bar." in column 14, line 16, and insert the following claim:

--7. A kit according to claim 5, wherein said differential pressure is less than 100 mbar.--

Column 14, line 43, cancel the text beginning with "18. A kit according" to and ending with "between 150 and 400." in column 14, line 46, and insert the following claims:

--18. A kit according to claim 1, wherein said ratio l/d is between 86 and 500.
  19. A kit according to claim 18, wherein said ratio l/d is between 150 and 400.--

Signed and Sealed this
Sixteenth Day of August, 2016

Michelle K. Lee
*Director of the United States Patent and Trademark Office*